United States Patent
Marsing et al.

(10) Patent No.: US 7,059,139 B1
(45) Date of Patent: Jun. 13, 2006

(54) SYSTEM FOR PREPARING CUTANEOUS TISSUE SAMPLES FOR ONCOLOGICAL HISTOLOGY STUDY AND DIAGNOSIS

(76) Inventors: Jacquelyn D. Marsing, 3562 E. Avondale Dr., Salt Lake City, UT (US) 84121; Richard Lynn Marsing, 3562 E. Avondale Dr., Salt Lake City, UT (US) 84121

( * ) Notice: Subject to any disclaimer, the term of this patent is extended or adjusted under 35 U.S.C. 154(b) by 0 days.

(21) Appl. No.: 09/075,063

(22) Filed: May 9, 1998

(51) Int. Cl.
*F25D 25/00* (2006.01)
*F25C 5/02* (2006.01)
*G01N 1/30* (2006.01)
*G01N 33/48* (2006.01)

(52) U.S. Cl. .............. 62/62; 62/320; 269/900; 269/909; 435/40.5

(58) Field of Classification Search .......... 62/62, 62/51.1, 331, 320; 435/40.5, 1.3; 356/36; 83/915.5; 269/909, 900

See application file for complete search history.

(56) References Cited

U.S. PATENT DOCUMENTS

| | | | | |
|---|---|---|---|---|
| 4,667,548 A | * | 5/1987 | Astle et al. | ............ 82/4 C |
| 5,188,347 A | * | 2/1993 | Hunnell et al. | ............ 269/258 |
| 5,533,342 A | * | 7/1996 | Gordon | ............ 62/51.1 |
| 5,550,033 A | * | 8/1996 | Krumdieck | ............ 435/40.52 |
| 5,628,197 A | * | 5/1997 | Rada | ............ 62/62 |
| 5,776,298 A | * | 7/1998 | Franks | ............ 156/390 |

* cited by examiner

*Primary Examiner*—William C. Doerrler
(74) *Attorney, Agent, or Firm*—Holland & Hart, LLP

(57) ABSTRACT

A method and apparatus for preparing tissue specimens for histological study utilizing two connectable sections each with hollowed cylinders for receiving first and second buttons, each button including planar disc and cylindrical stem portions, such that the stem portions can be slideably mounted in hollowed cylinders. The planar disc portions of the buttons are capable of receiving tissue specimens.

13 Claims, 5 Drawing Sheets

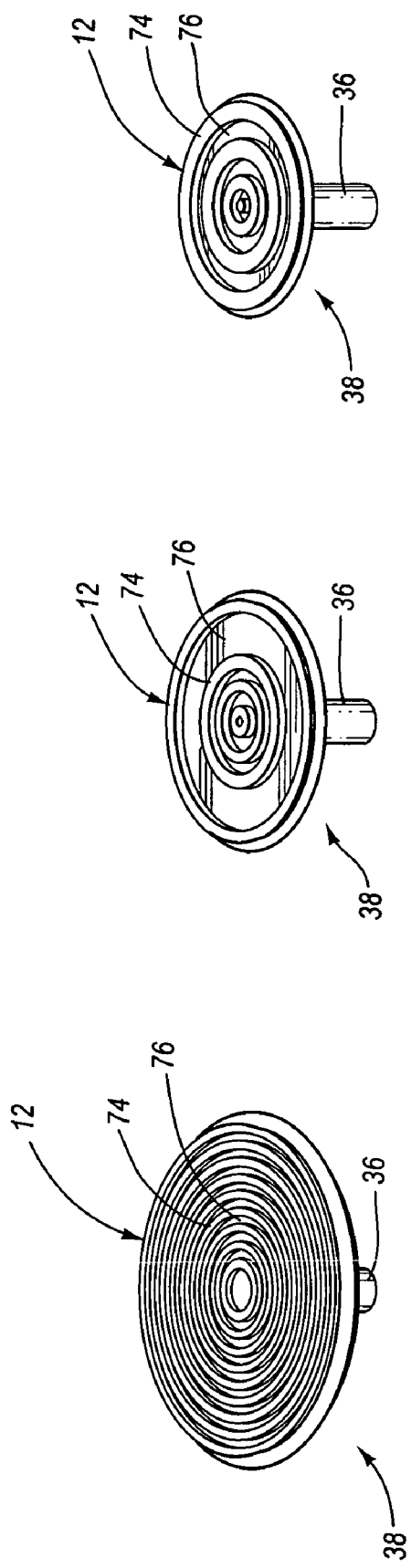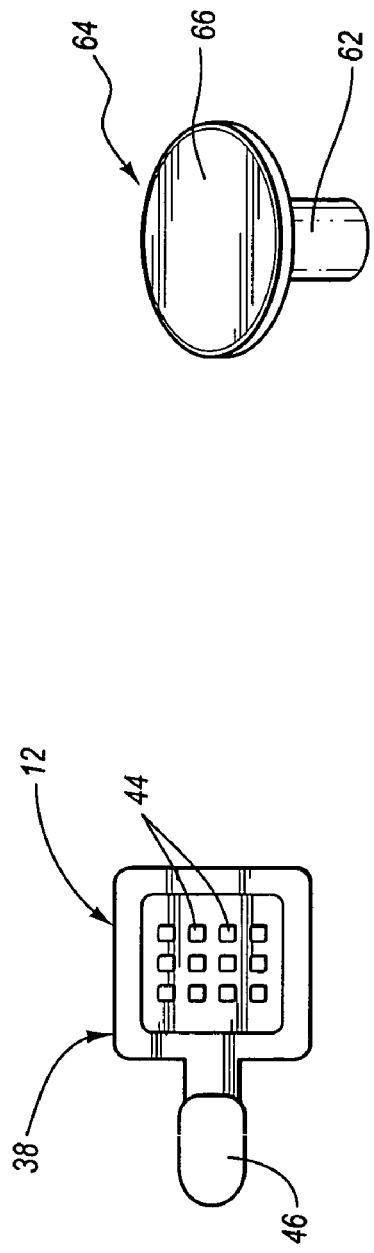

SYSTEM FOR PREPARING CUTANEOUS TISSUE SAMPLES FOR ONCOLOGICAL HISTOLOGY STUDY AND DIAGNOSIS

TECHNICAL FIELD OF THE INVENTION

This invention relates generally to the field of medical diagnostic equipment and methods, and more specifically to a novel system, including devices and methods, for preparing cutaneous tissue samples for oncological histology study and diagnosis. The system offers the advantages of observing conservation of tissue, while at the same time enjoying quick and precise tissue sample preparation, which in turn allows immediate and accurate diagnosis of existing malignant conditions.

BACKGROUND OF THE INVENTION

There are currently numerous methods for preparing cutaneous tissue samples for diagnosis of various malignancies. In most instances, tissue samples are removed from the patient, packaged and then sent to a laboratory where tests are made, usually at a location remote from where the sample was taken. Thus, travel time for the sample between the operating room and the laboratory can delay an important diagnosis for several days or even weeks. Such an inordinate amount of time can be pivotal in the diagnosis and treatment of some of the more serious types of skin cancer.

By way of analogy, skin cancer develops much like the roots of a tree. These roots may extend horizontally, just beneath the surface, or they may invade the deeper tissues in a vertical pattern. Just as it is difficult to accurately determine the extent of its root system by studying the visible 5 portions of a tree, so it is with cutaneous carcinomas; small tumors may have deep roots, and very large tumors may have shallow, superficial roots.

Furthermore, the nature of a tree's root system is influenced by its genetic make-up, the soil in which it grows, and its supply of water and nutrition. With skin cancer, numerous factors of a similar nature effect its growth, such as location, blood supply, and the innate ability of the host to resist the growth of the tumor.

A number of treatment methods, including x-ray, surgery, electrosurgery and cryosurgery have been used effectively in treating skin cancers. However, these methods will fail if roots are left behind, thus allowing the tumor to return by regrowing at a later date. The problem is that the roots of a skin tumor are so small that they can only be seen with the aid of a microscope. Therefore, it is logical that a microscope be used to avoid leaving any of the cancer behind.

For these reasons, the Mohs technique was developed. The Mohs procedure allows the surgeon to excise a sample of cancerous tissue and systematically examine by microscope the undersurface of the margins by frozen sections, map the location of the residual tumor, and reexcise and reexamine subsequent layers of tissue until a cancer-free plane is reached. Since examination and diagnosis of the excised tissue are performed on site immediately after the sample is taken, it usually allows the patient to remain in the hospital or clinic until all cancerous tissue has been removed.

The Mohs technique is widely considered the most effective method for treating primary cutaneous malignancies and almost all recurrent, nonmetastic tumors. Because the surgeon can accurately identify tumor roots, or extensions, microscopically, residual clinically undetectable cancerous tissue can be removed, and normal tissue, ordinarily unnecessarily sacrificed by conventional surgery or irradiation, can be spared.

In the Mohs technique, cutaneous tissue specimens are removed by the surgeon in thin layers surrounding areas where a tumor is evident. The first micrographic layer that is removed includes all the clinically evident tumor plus a small peripheral margin of normal appearing tissue. The surgeon immediately diagrams the tissue specimen and applies various colored dyes to the edges of the tissue specimen for later orientation and identification.

The specimen is then placed upside down (epidermal or outermost surface down) onto a cryostat button. In this orientation, the deepest cutaneous layers will be the first layers sectioned, thereby theoretically allowing the lateral and deep margins of the tissue to be examined in the same plane under the microscope. As the specimen is placed on the button, the technician or user must continually attempt to flatten the lower or exposed surface of the specimen. If he or she is unsuccessful at flattening the lower surface, it will not be possible to section the specimen in such a way that an entire plane of tissue can be viewed through the microscope at one time. If an entire plane cannot be viewed simultaneously, there is a substantial risk that the sectioned specimen will provide inaccurate data and therefore that the surgeon or pathologist will be unable to properly diagnose the condition.

Once the tissue specimen has been properly placed on the button in an upside down orientation, it is frozen using standard cryostat microtome freezing techniques. The most common cryostat microtome freezing technique requires that the tissue specimen be surrounded by an imbedding medium such as OCT Compound. The specimen and embedding medium are then immediately saturated with a quick freezing compound such as Fisherbrand Histofeeze 2000. Other techniques involve freezing the specimen using an albumin solution and carbon dioxide. During the freezing procedure it is common for the technician to place the button upside down inside the cryostat on a device known generically as a cold plate. The cold plate holds the button and tissue specimen until the technician is ready to begin sectioning.

During the freezing procedure under current techniques, the tissue specimen is not held in place on the button and as a result has a tendency to move relative thereto. As indicated above, if such movement and the specimen is improperly placed on the button, there is a substantial risk that the sectioned specimen will provide inaccurate data and that the surgeon or pathologist will be unable to properly diagnose the condition.

Additionally, during the freezing procedure the sides of the tissue specimen have a tendency to droop towards the surface of the button. The technician must constantly use a scalpel or other device to lift the edges of the tissue specimen away from the surface of the button and attempt to maintain the tissue specimen in a flat orientation. If the technician cannot accomplish this two fold task during the freezing procedure, the specimen must be thawed and the whole freezing procedure must be repeated.

SUMMARY OF THE INVENTION

In light of the problems addressed above, as well as others that are known to those skilled in the art and others that will become apparent, the present invention seeks to accomplish and realize, among other things, the following objects and advantages.

A principal objective of this invention is the provision of a system that operates as an adjunct to the Mohs technique for simultaneously diagnosing and treating cutaneous malignancies, such as skin cancer.

Another major objective of the present invention is to provide a system whereby a cutaneous tissue specimen is mounted for diagnostic sectioning in a manner that is more accurate and less time consuming than hitherto known.

Yet another important objective is the provision of a system that supplements the well-known Mohs technique without interfering with its purposes and established procedures.

Still a further main objective of the current invention is to provide a novel system, including devices and methods, which conserves the amount of tissue removed from a patient experiencing skin cancer, thereby leaving the patient with a minimal wound.

Another principal objective of this invention is the provision of an accurate, precise and consistent manner of freezing cutaneous tissue samples for oncological histology study and diagnosis.

Yet a further important objective of the present invention is to satisfy the need for a system for maintaining the deepest cutaneous layers in a single, consistent plane, thus providing a tissue specimen that allows a surgeon or pathologist to quickly and accurately diagnose the condition, as well as its extent.

Still another major objective of this invention is to provide a method, and attendant devices, that prevents portions of a tissue sample from distorting in shape as it is manipulated and frozen in preparation for sectioning, the result being an accurate and dependable cross section of problem areas.

An additional objective is to provide a device that secures a specimen in place during the freezing procedure by preventing movement of the tissue specimen relative to the button upon which it is mounted.

One more significant objective of this invention is the provision of a device which eliminates, or substantially alleviates, the need to thaw and refreeze improperly prepared tissue specimens due to operator error, thereby preserving the specimens and preventing damage thereto which could cause the surgeon or pathologist to inaccurately diagnose the patient's condition.

These and other objects and advantages of the invention will become more fully apparent from the description and claims which follow, or may be learned by the practice of the invention. The preferred system for preparing cutaneous tissue specimens for oncological histology study and diagnosis comprises generally a device adapted to aid in properly mounting a tissue specimen onto a button, the tissue and button to be mounted in a cryostat and the tissue to be sectioned into thin layers in order to provide an accurate representation of the afflicted area; a first holding plate disposed within the cryostat, the first holding plate for storing multiple buttons containing specimens; and a second holding plate disposed outside the cryostat, the second holding plate including a storage area for buttons, as well as a cutting board for initial preparation of a specimen.

The device itself comprises first and second corresponding temporarily connectable sections, the first section including a first mounting system for temporarily securing a first button to the device. Preferably, the first mounting system includes an adapting system for facilitating the temporary securement of the first button to the first section of the device using the first mounting system. The preferred adapting system comprises an adapter, which has a planar portion and a stem portion, the planar portion being shaped and otherwise adapted to receive and temporarily secure the first button.

The stem portion of the adapter is advantageously adapted to be slideably received and therefore temporarily secured by a first hollowed cylinder in the first section which comprises the first mounting system. More specifically, the stem portion of the adapter includes a hollowed cylinder, while the first button comprises a planar disc portion and a cylindrical stem portion, such that stem portion of the first button is slideably secured in the hollowed cylinder of the stem portion of the adapter.

Alternatively, the planar portion of the adapting system includes a rectilinear ridged plate having at least one notch in the ridges. This configuration allows for use of a slightly varied brand of button to be used by the system, this particular brand providing a square shaped button with an outwardly extending stem or handle. An adapting system is preferred because it allows the use of virtually all brands of buttons with the system. However, it is to be realized that certain makes of buttons have stems that fit perfectly within the hollowed cylinder of the first mounting system; in this instance, the need for an adapting system is obviated.

Returning now to the first and second holding plates, it is preferred that the first holding plate including a second mounting system, the second system comprising at least one, but advantageously multiple, hollowed cylinders bored into the first plate and adapted to slideably receive and secure the first button to the first holding plate, a tissue specimen having been mounted on the first button. As indicated above, the first holding plate is designed to reside within the cryostat, thus allowing tissue specimens mounted thereon to be preserved.

The second holding plate, on the other hand, is designed to reside outside the cryostat. It comprises a third mounting system for temporarily securing a second button and a cutting board, where initial preparation of the tissue specimen is accomplished. As with the other mounting systems, the third mounting system preferably comprises at least one, but advantageously multiple, hollowed cylinders bored into the second plate and adapted to slideably receive and secure a number of second buttons in preparation for beginning the process of using the system.

As mentioned above, the device further comprises a second button, which corresponds to the first button, and, just as the first button, includes both a planar disc portion and a cylindrical stem portion. The second section of the device comprises a fourth mounting system for temporarily securing the second button to the device, the fourth mounting system being a second hollowed cylinder, thereby allowing the stem portion of the second button to be slideably secured in the second section of the device. Preferably, the first and second buttons, when mounted in their respective mounting systems in their respective sections, are axially aligned and disposed such that their respective planar portions are parallel to each other and, during use, the tissue specimen is disposed therebetween.

Further, the first and second buttons are both adapted to receive tissue specimens on their respective planar disc portions. Importantly, however, the planar disc portions of the first and second buttons are different. Specifically, the planar disc portion of the first button has an uneven surface in order to better grip the specimen, while the planar disc portion of the second button has a smooth and even surface. Advantageously, the uneven surface of the first button is organized into a plurality of ridges and furrows, preferably arranged in a circular pattern. Alternatively, this uneven surface is organized into a pattern of raised squares. Finally, in order to distinguish between tissue specimens and thus avoid losing track thereof, the first buttons may be color coded.

It is preferred that the first and second sections of the device include longitudinal grooves placed so as to facilitate the grasping of the device by the user. Also, as indicated, the first and second sections of the device correspond to each other and are temporarily connectable. In order to facilitate this criteria, the first section has a plurality of posts and the second section has an aperture which corresponds to each post, such that when the posts of the first section are inserted into the apertures of the second section, a temporary connection of the sections is provided. In its preferred embodiment, this temporary connection brings the first and second buttons into axial alignment with each other, their planar disc portions being parallel to each other with, the tissue specimen disposed in between.

DESCRIPTION OF THE DRAWINGS

In order that the manner in which the above-recited and other advantages and objects of the invention can be appreciated, a more particular description of the invention briefly described above will be rendered by reference to a number of specific embodiments which are illustrated in the appended drawings. Understanding that these drawings depict only typical embodiments of the invention and are not to be considered limiting in scope, the invention will be described and explained with additional specificity and detail through the use of accompanying drawings, in which:

FIGS. 7A through 7E are perspective views of different types of buttons.

DETAILED DESCRIPTION OF THE INVENTION

Reference is now made to the drawings, wherein like numerals are used to designate like components throughout. The preferred system for preparing cutaneous tissue specimens for oncological histology study and diagnosis comprises generally a device 10 adapted to aid in the proper mounting of a tissue specimen A onto a first button 12, a first holding plate 14 to be disposed within the cryostat (not shown), and a second holding plate 16 to be disposed outside the cryostat. Each of these components will be described in more intimate detail hereafter.

Figure 2:
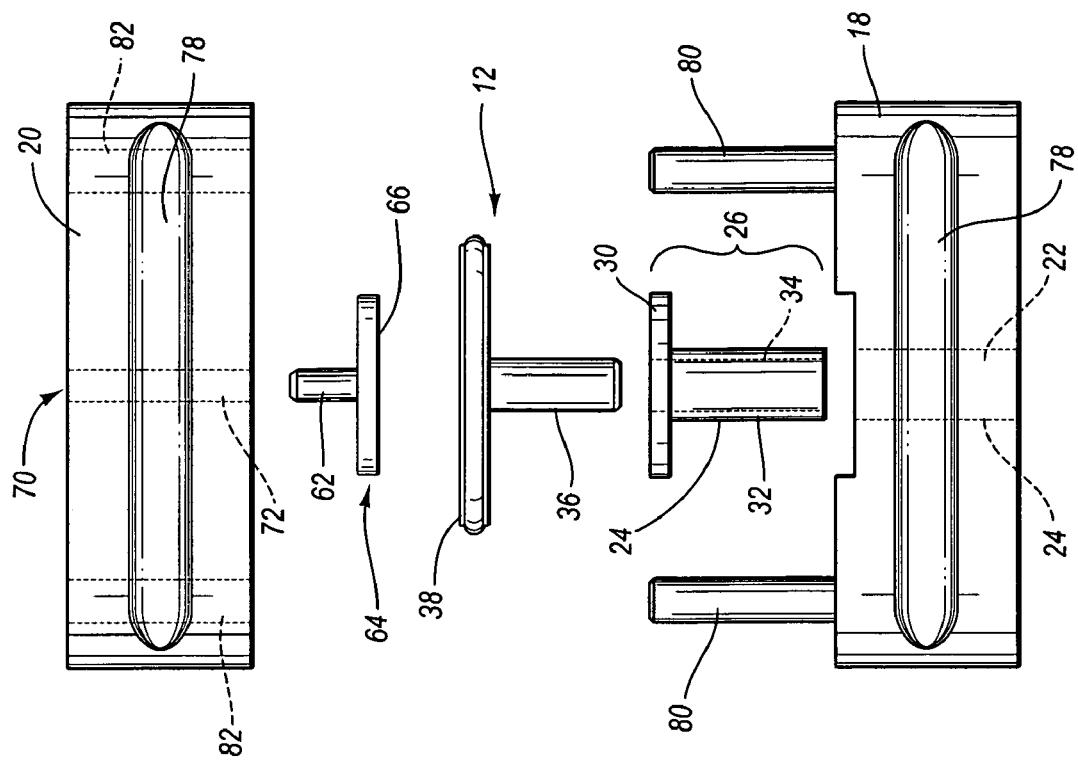
FIG. 2 is an exploded side elevational view of the device, according to the embodiment of FIG. 1.
Figure 1:
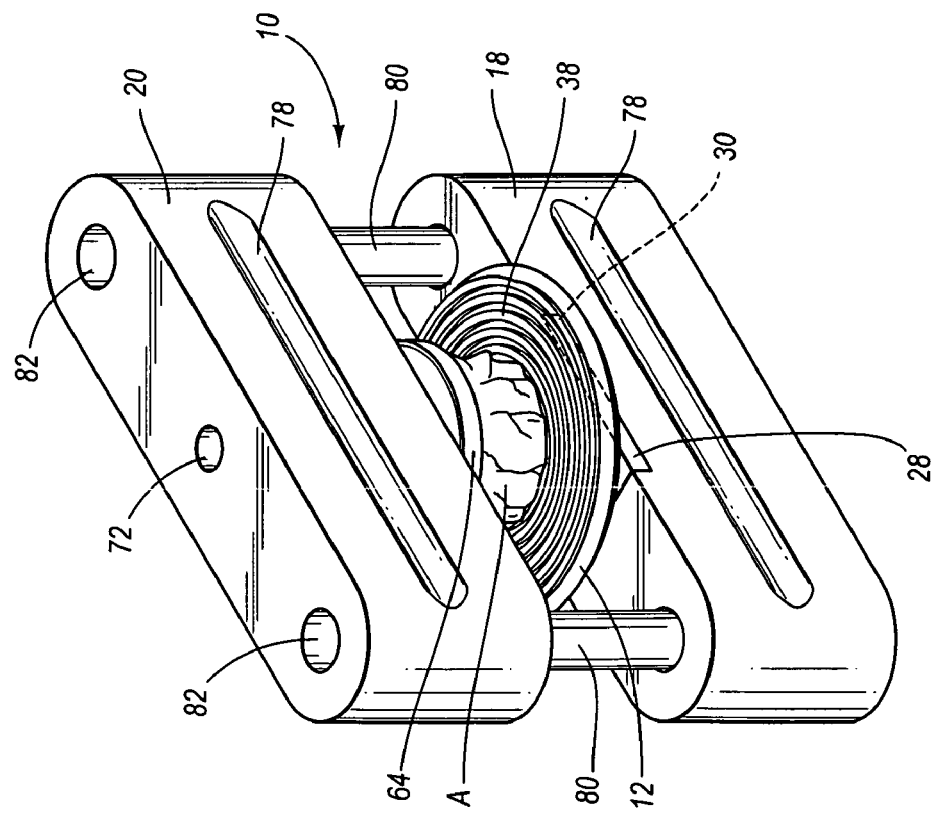
FIG. 1 is a perspective view of an embodiment of the device.

Referring initially to FIGS. 1 and 2, the device 10 is illustrated as comprising first and second corresponding sections 18 and 20, respectively, which are temporarily connectable together. The first section 18 includes a first hollowed cylinder 22 bored therethrough, which is included in a first mounting system 24. The first mounting system 24 is for temporarily securing the first button 12 to the first section 18 of the device 10, and further includes an adapting system 26 for facilitating the temporary securement of the first button 12.

Figure 8A:
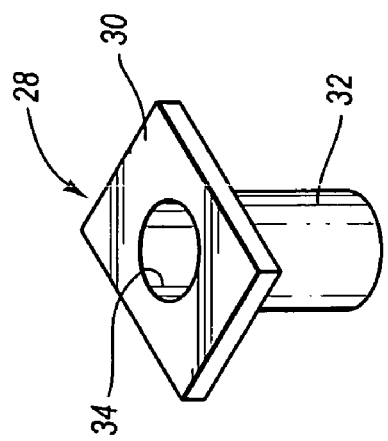
FIGS. 8A through 8C are perspective views of different types of adapters.
Figure 8B:
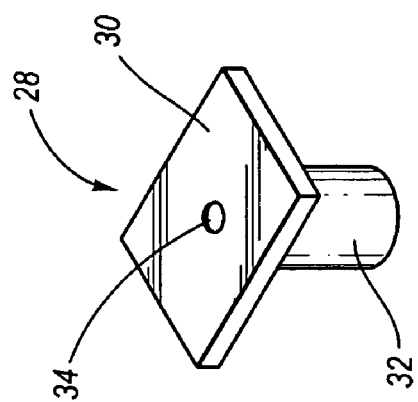
Figure 8C:
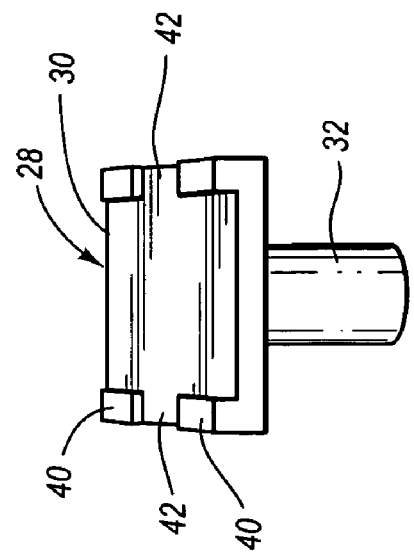

The adapting system comprises an adapter 28, which has a planar portion 30 and a stem portion 32, the planar portion 30 being shaped and otherwise adapted to receive and temporarily secure the first button 12, while the stem portion 32 is shaped and sized so as to be slideably received and therefore temporarily secured by the first hollowed cylinder 22 of the first mounting system 24. See FIG. 2. As shown in FIGS. 8A through 8C, the outside diameter of the stem portion 32 is about the same as the inside diameter of the first hollowed cylinder 22 in order that slideable reception and securement can occur.

The stem portion 32 of the adapter 28 may further include a hollowed cylinder or bore 34, as seen in FIGS. 8A and 8B, which is sized to slideably receive the stem portion 36 of the first button 12, the first button 12 comprising a planar disc portion 38, as well as the stem portion 36. Alternatively, as illustrated in FIG. 8C, a bore 34 is not necessary, in which case the planar portion 30 of the adapter 28 is rectilinear in shape and includes ridges 40 about at least some of its edges, as well as at least one notch 42.

This particular configuration of the adapter 28 is designed to accommodate a square shaped first button 12, which is shown to have raised squares 44 on its surface to facilitate in the gripping of the tissue specimen A and an outwardly extending handle 46. See FIG. 7D. As illustrated, this particular first button 12 fits snugly onto the planar portion 30 of the adapter 28, such that its ridges 40 encompass the planar disc portion 38 of the first button 12. Furthermore, the handle 46 is designed to rest in the notch 42.

Figure 3:
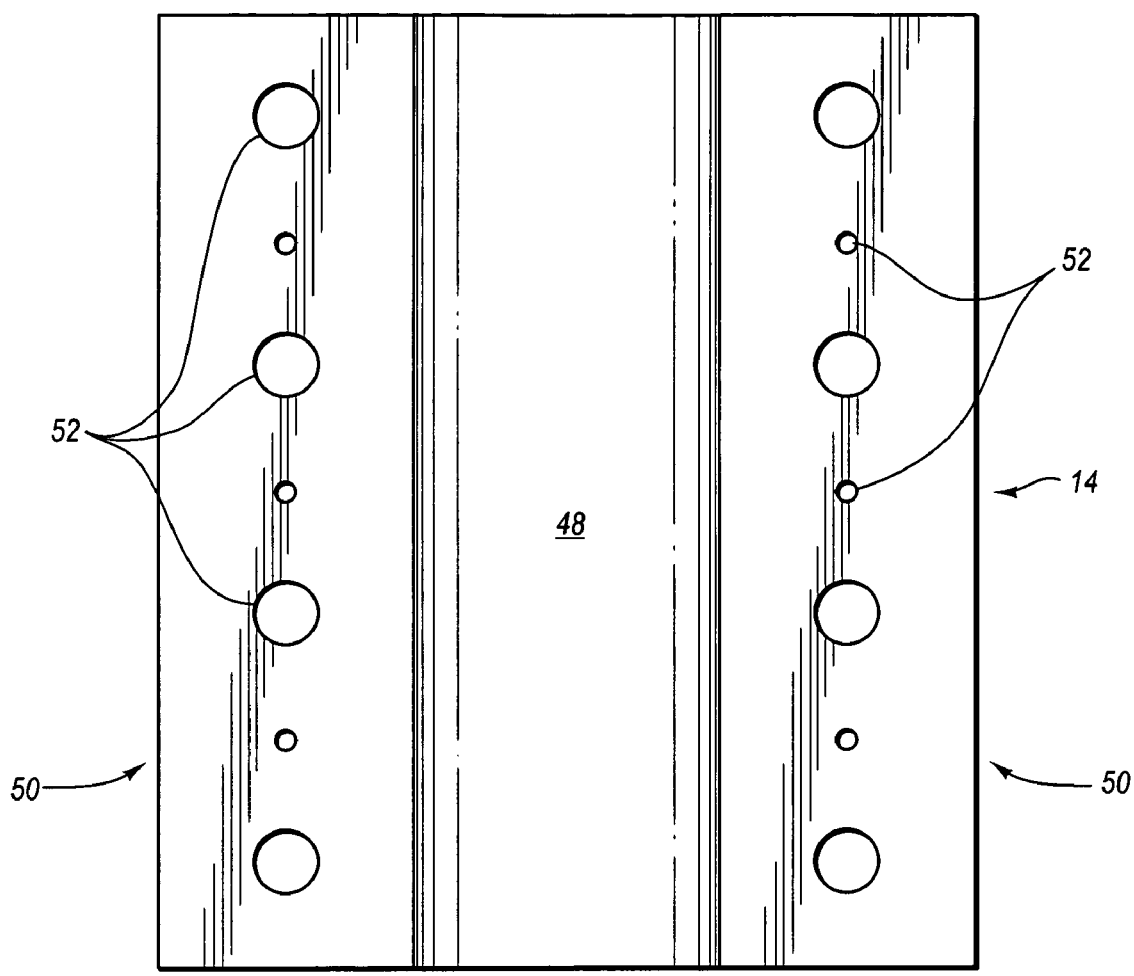
FIG. 3 is a top view of a first holding plate.
Figure 4:
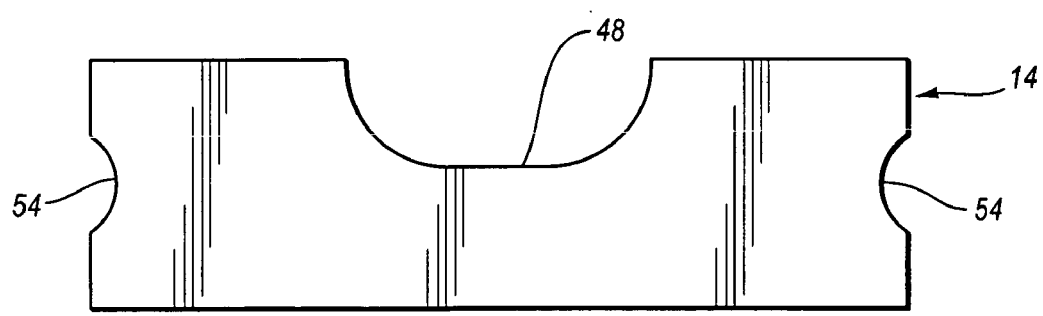
FIG. 4 is a side elevational view of the first holding plate.

Referring now to FIGS. 3 and 4, the preferred first holding plate 14 is shown in some detail. As indicated, the holding plate 14 is disposed within the cryostat during use and thus remains cold. The holding plate 14 comprises a single block of material, such as aluminum, from which a lengthwise trough 48 is cut. Also, the first holding plate 14 includes a second mounting system 50 arranged about the edges of the trough 48. The second mounting system 50 includes a plurality of hollowed cylinders or bores 52 of varying diameter to accommodate varying sizes of stem portions 36 of first buttons 12. Advantageously, longitudinal grooves 54 are cut into the sides of the first holding plate 14 in order to facilitate grasping of the device by the user.

Figure 5:
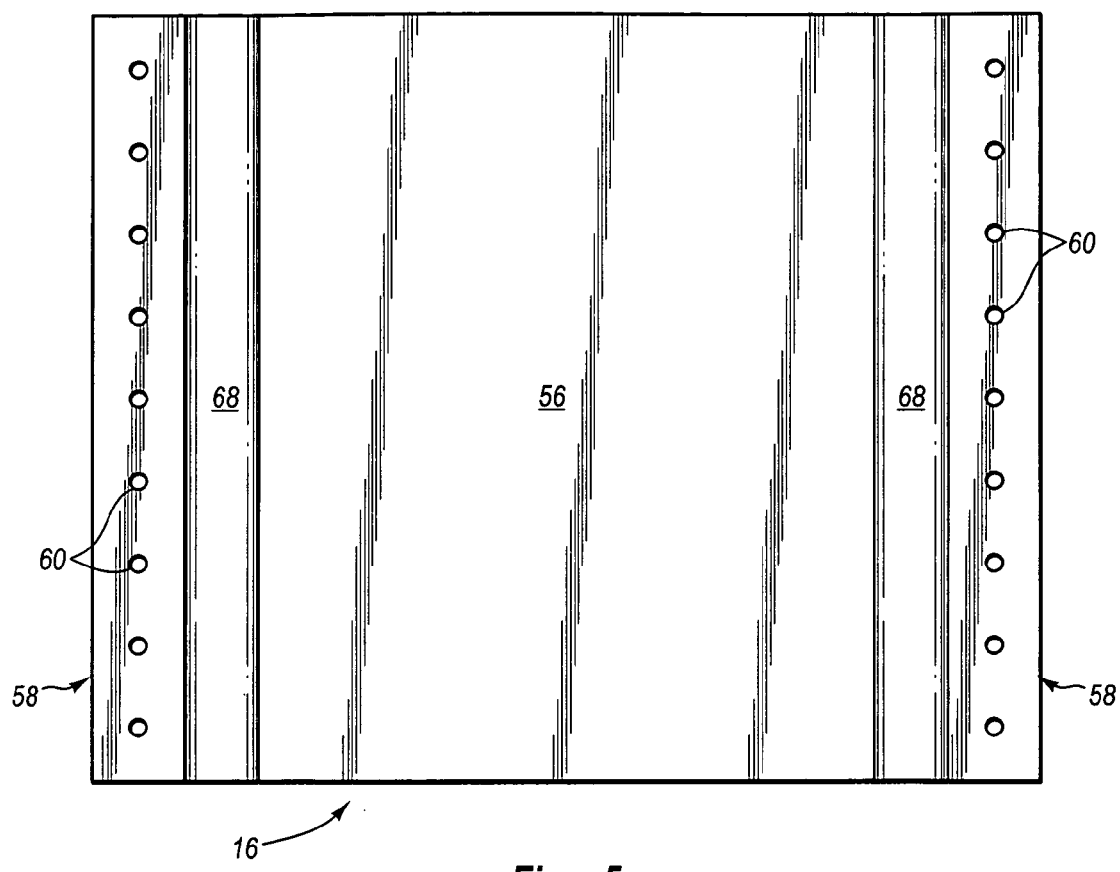
FIG. 5 is a top view of a second holding plate.
Figure 6:
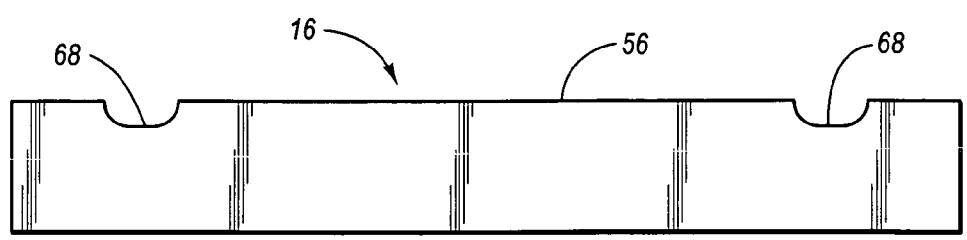
FIG. 6 is a side elevational view of the second holding plate.

FIGS. 5 and 6 illustrate the second holding plate 16, which comprises a cutting board 56 surrounded by a third mounting system 58, which includes, as the second mounting system, a plurality of hollowed cylinders or bores 60, into which the stem portion 62 of a second button 64 is inserted to maintain and store extra second buttons 64 in anticipation of use. The second button 64 further includes a planar disc portion 66, which, as with the first button 12, is adapted to receive the tissue specimen A. Also, the second holding plate 16 comprises two troughs 68, which serve to facilitate the handling of the second buttons 64 stored there.

Returning now to the device 10, the second section 20 comprises a fourth mounting system 70, which is similar to the first mounting system 24 in that it includes a hollowed cylinder 72 drilled through the second section 20, although the hollowed cylinder 72 is sized so as to accommodate and slideably receive only the second button 64, which has a standard size. Therefore, the adapting system 26 is not needed in conjunction with the fourth mounting system 70.

The preferred second button 64 is shown in FIG. 7E and has a smooth and even planar disc portion 66. This is a contrast to the preferred first button 12, embodiments of which are illustrated in FIGS. 7A through 7D. As indicated, the planar disc portion 38 of the first button 12 is uneven and comprises either a series of ridges 74 and furrows 76, or a plurality of raised squares 44, as in the embodiment shown in FIG. 7D. Advantageously, the first buttons 12 may be color coded in to distinguish between different specimens.

As clearly, shown in the drawings, the first and second sections 18 and 20 are block-like in shape and may be constructed from a single piece of aluminum or similar material. The sections 18 and 20 of the device 10 include longitudinal grooves 78 along their sides in order to facilitate the handling thereof. The first section 18 includes a plurality of posts 80 and the second section includes for each post 80 a corresponding aperture or hollowed receiving cylinder 82, thereby allowing temporary connection of the two sections 18 and 20. In this manner, the first and second buttons 12 and 64, respectively, may be brought into axial alignment and their respective planar disc portions 38 and 66 may be brought into a parallel position with the specimen A being disposed therebetween. See FIG. 1.

In use, the surgeon excises a tissue specimen A from a patient, the tissue specimen A being brought into an environment containing the system of the present invention, as well as a standard cryostat. Initially, the specimen A is scored with a scalpel and otherwise manipulated on the cutting board 56. The operator then removes a second button 64 from the fourth mounting system 70 and mounts the specimen A thereon, using a freezing agent, the deepest portion of the tissue specimen A being in contact with the second button 64.

The user then mounts the second button 64 onto the second section 20 of the device 10 and mounts a first button 12 onto the first section 18 of the device 10. The two sections 18 and 20 are then temporarily connected by using the corresponding posts 80 and apertures 82, thereby bringing the specimen A into contact with both buttons 12 and 64 simultaneously, while additional freezing occurs. In this manner, the specimen A is not allowed to distort as it is frozen in order that improved representations may be made.

Next, the two buttons 12 and 64 are removed from the device 10 and the second button 64 is removed froth contacting the specimen A by the use of a blade (not shown). Because of this step in the procedure, the planar disc portion 66 of the second button 64 is smooth and even. Meanwhile, the specimen remains properly mounted on the first button 12 in a frozen state. In this condition the first button 12 and specimen A are either mounted onto the first holding plate 14 in the cryostat in order to become even more frozen, or, if sufficiently frozen, they may be mounted onto cutting facility of the cryostat so that thin representative layers may be cut and examined by the surgeon or pathologist so that a diagnosis can be made.

This invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A device for aiding in the preparation of cutaneous tissue specimens for oncological histology study and diagnosis, the device comprising:

first and second corresponding temporarily connectable sections, the first section including a first hollowed cylinder and the second section including a second hollowed cylinder, and first and second buttons, each button including a planar disc portion and a cylindrical stem portion, such that the stem portion of the first button can be slideably mounted in the first hollowed cylinder and the stem portion of the second button can be slideably mounted in the second hollowed cylinder, the planar disc portions of the buttons being adapted to receive the tissue specimen.

2. A device for aiding in the preparation of cutaneous tissue specimens for oncological histology study and diagnosis, according to claim 1, wherein the planar disc portion of the first button includes an uneven surface for gripping the specimen.

3. A device for aiding in the preparation of cutaneous tissue specimens for oncological histology study and diagnosis, according to claim 2, wherein the uneven surface includes ridges and furrows.

4. A device for aiding in the preparation of cutaneous tissue specimens for oncological histology study and diagnosis, according to claim 3, wherein the ridges and furrows are organized in a circular pattern.

5. A device for aiding in the preparation of cutaneous tissue specimens for oncological histology study and diagnosis, according to claim 2, wherein the uneven surface includes a pattern of raised squares.

6. A device for aiding in the preparation of cutaneous tissue specimens for oncological histology study and diagnosis, according to claim 1, the first and second sections further including longitudinal grooves for facilitating the grasping of the device by the user.

7. A device for aiding in the preparation cutaneous tissue specimens for oncological histology study and diagnosis, according to claim 1, the first section including a plurality of posts and the second section including a corresponding aperture for each post, such that when the posts are inserted into the corresponding apertures, a temporary connection is provided.

8. A device for aiding in the preparation of cutaneous tissue specimens for oncological histology study and diagnosis, according to claim 7, wherein the temporary connection of the first and second sections brings the first and second buttons into alignment, such that the planar disc portions are parallel to each other and the tissue specimen is disposed therebetween.

9. A device for aiding in the preparation of cutaneous tissue specimens for oncological histology study and diagnosis, according to claim 1, further including adapting means for facilitating the temporary securement of the first button to the first section.

10. A device for aiding in the preparation of cutaneous tissue specimens for oncological histology study and diagnosis, according to claim 9, wherein the adapting means includes a planar portion and a stem portion, the planar portion being adapted to receive and temporarily secure the first button, and the stem portion being adapted to be received and temporarily secured by the first hollowed cylinder of the first section.

11. A device for aiding in the preparation of cutaneous tissue specimens for oncological histology study and diagnosis, according to claim 1, wherein the planar disc portion of the second button includes a smooth surface.

12. A device for aiding in the preparation of cutaneous tissue specimens for oncological histology study and diagnosis, according to claim 1, wherein the buttons are color coded to distinguish between tissue specimens.

13. A method of preparing a cutaneous tissue specimen for oncological histology study and diagnosis, the method including the steps of:
   a) placing an excised tissue specimen on the smooth planar disc portion of the second of two buttons, with the deepest tissue layers in contact with the second button,
   b) slideably mounting the first and second buttons to first and second corresponding temporarily connectable sections, respectively,
   c) temporarily connecting the corresponding first and second sections, thereby aligning the buttons and bringing the tissue specimen into contact with the first button,
   d) freezing the tissue specimen,
   e) dismounting the first and second buttons,
   f) removing the second button from the tissue specimen, and sectioning the tissue specimen in a cryostat.

* * * * *